United States Patent
Friedt et al.

(10) Patent No.: US 11,185,887 B2
(45) Date of Patent: Nov. 30, 2021

(54) ACOUSTIC WAVE H2S SENSOR COMPRISING A POLYMER FILM COMPRISING CARBOXYLATE FUNCTIONAL GROUPS AND LEAD OR ZINC CATIONS AND MANUFACTURING PROCESS

(71) Applicants: SENSEOR, Valbonne (FR); CENTRE NATIONAL DE LA RECHERCHE SCIENTIFIQUE, Paris (FR); TOTAL SA, Courbevoie (FR); UNIVERSITE DE FRANCHE-COMTE, Besancon (FR)

(72) Inventors: Jean-Michel Friedt, Besancon (FR); Frédéric Cherioux, Larnod (FR); Simon Lamare, Coulanges les Nevers (FR); François Gegot, Besancon (FR)

(73) Assignees: SENSEOR, Valbonne (FR); CENTRE NATIONAL DE LA RECHERCHE SCIENTIFIQUE, Paris (FR); TOTAL SA, Courbevoie (FR); UNIVERSITE DE FRANCHE-COMTE, Besancon (FR)

( * ) Notice: Subject to any disclaimer, the term of this patent is extended or adjusted under 35 U.S.C. 154(b) by 255 days.

(21) Appl. No.: 15/702,652

(22) Filed: Sep. 12, 2017

(65) Prior Publication Data
US 2018/0071780 A1    Mar. 15, 2018

(30) Foreign Application Priority Data
Sep. 13, 2016   (FR) ...................................... 1658487

(51) Int. Cl.
*G01N 33/00* (2006.01)
*B06B 1/06* (2006.01)
(Continued)

(52) U.S. Cl.
CPC .......... *B06B 1/0662* (2013.01); *B06B 1/0261* (2013.01); *B32B 27/308* (2013.01);
(Continued)

(58) Field of Classification Search
CPC .................................................... B06B 1/0662
(Continued)

(56) References Cited

U.S. PATENT DOCUMENTS

| 3,167,734 A | 1/1965 | Brucken et al. |
| 5,034,452 A | 7/1991 | Kunz |

(Continued)

OTHER PUBLICATIONS

W.P. Jakubik et al., "Polyaniline Thin Films as a Toxic Gas Sensors in Saw System," Molecular and Quantum Acoustics, vol. 28, 2007, pp. 125-129.
(Continued)

*Primary Examiner* — Christine T Mui
*Assistant Examiner* — Emily R. Berkeley
(74) *Attorney, Agent, or Firm* — BakerHostetler (57) ABSTRACT

An $H_2S$ sensor includes at least one acoustic wave transducer and a film having a polymer matrix. The polymer matrix includes carboxylate functional groups and lead or zinc cations. The film may have a thickness of between a hundred nanometres and a 2 microns The $H_2S$ sensor optionally includes an antenna to remotely interrogate the $H_2S$ sensor.

17 Claims, 3 Drawing Sheets

(51) Int. Cl.
  *G01N 29/02* (2006.01)
  *G01N 29/036* (2006.01)
  *B06B 1/02* (2006.01)
  *B32B 27/30* (2006.01)
  *B32B 27/34* (2006.01)
  *B32B 27/36* (2006.01)
  *B32B 27/40* (2006.01)
  *G01N 29/24* (2006.01)
  *C01G 9/00* (2006.01)
  *C01G 21/00* (2006.01)
  *C08L 33/06* (2006.01)
  *C08L 75/04* (2006.01)

(52) U.S. Cl.
  CPC ............ *B32B 27/34* (2013.01); *B32B 27/365* (2013.01); *B32B 27/40* (2013.01); *G01N 29/022* (2013.01); *G01N 29/036* (2013.01); *G01N 29/2412* (2013.01); *G01N 33/0044* (2013.01); *C01G 9/00* (2013.01); *C01G 21/00* (2013.01); *C08L 33/06* (2013.01); *C08L 75/04* (2013.01); *G01N 2291/014* (2013.01); *G01N 2291/0255* (2013.01); *G01N 2291/0256* (2013.01)

(58) Field of Classification Search
  USPC .......................................................... 436/121
  See application file for complete search history.

(56) References Cited

U.S. PATENT DOCUMENTS 5,910,286 A * 6/1999 Lipskier ............... G01N 29/022
                                        422/68.1
6,773,926 B1 * 8/2004 Freund .................. G01N 31/22
                                        436/111

OTHER PUBLICATIONS

M. Asad et al., "Surface acoustic wave based H2S gas sensors incorporating sensitive layers of single wall carbon nanotubes decorated with Cu nanoparticles," Sensors and Actuators B: Chemical, vol. 198, 2014, pp. 134-141.

Hanming Ding et al., "Detection of hydrogen sulfide: the role of fatty acid salt Langmuir-Blodgett films," Materials Science and Engineering, vol. 11, No. 2, Nov. 28, 2000, pp. 121-128, XP055363717.

G. Dzhardimalieva et al., "Macromolecular metal carboxylates," Russian Chemical Reviews, vol. 77, No. 3, Mar. 31, 2008, pp. 259-301, XP055364214.

Zainab Yunusa et al., "Gas Sensors: A Review," Sensors & Transducers, Apr. 30, 2014, pp. 61-75, XP055363935.

T. Ding et al., "Synthesis of HgS and PbS nanocrystals in a polyol solvent by microwave heating," Microelectronic Engineering, vol. 66, 2003, pp. 46-52.

H. Karami et al., "Synthesis, characterization and application of lead sulfide nano-structures as ammonia gas sensing agent," Int. J. Electrochem. Sci., vol. 8, 2013, pp. 11661-11679.

Z. Zeng et al., "Synthesis and characterization of PbS nanocrystallites in random copolymer ionomers," Chem. Materials, vol. 11, 1999, pp. 3365-3369.

W. Wang et al., "Wireless surface acoustic wave chemical sensor for simultaneous measurement of CO2 and humidity," J. Micro/Nanolith, MEMS MOEMS, vol. 8, No. 3, 2009, 031306.

D. Rabus et al., "A high sensitivity open loop electronics for gravimetric acoustic wave-based sensors," IEEE Trans. UFFC, 2013, vol. 60, No. 6, pp. 1219-1226.

* cited by examiner

ACOUSTIC WAVE H2S SENSOR COMPRISING A POLYMER FILM COMPRISING CARBOXYLATE FUNCTIONAL GROUPS AND LEAD OR ZINC CATIONS AND MANUFACTURING PROCESS

CROSS-REFERENCE TO RELATED APPLICATIONS

This application claims priority to foreign French patent application No. FR 1658487, filed on Sep. 13, 2016, the disclosure of which is incorporated by reference in its entirety.

FIELD OF THE INVENTION

The field of the invention is that of the detection of hydrogen sulfide present in the gas or liquid phase and regarded, in its first form, as toxic for concentrations of the order of 20 ppm. Produced in particular by bacteria which contaminate oil boreholes, its detection can represent a major challenge.

The known art in this field provides a certain number of solutions (electrochemical, colourimetric, conductimetric) incompatible with the deployment of a passive autonomous sensor which can be remotely interrogated without a wire-based link, for example by a radiofrequency link.

BACKGROUND

In this context, the Applicants have looked for a solution which makes it possible in particular to functionalize an acoustic wave piezoelectric transducer, making it possible to prepare a sensor compatible with the absence of a local energy source and with wireless remote measurements.

The Applicants have thus prepared a film of material sensitive to $H_2S$ which can be produced reproducibly, and of controlled thickness, which can in particular be used in a passive sensor propagating an acoustic wave making possible the detection of the presence of $H_2S$ in the form of a weight of gas absorbed on the surface.

Broadly, a film of sensitive material of controlled thickness can be made use of with any transducer having direct detection (for example, optical detection or detection by surface plasmon resonance).

Generally, remotely interrogatable acoustic wave passive sensors comprising a sensitive layer making it possible to detect certain types of compounds are already known. The weight captured is able to induce a variation in the limiting conditions of propagation of the acoustic wave; conventionally, it is a slowing down in the wave, observed as a decrease in the phase of the radiofrequency signal exciting the transducer.

In the context of the present invention, the Applicants have in particular designed a passive sensor using an acoustic wave transducer of the known art and have functionalized it with a layer containing reactive sites in order to add, to the conventional transducer, a sensitivity specific to $H_2S$.

In order to do this, the Applicants have sought to make use of a compound known for its selective reaction with the element sulfur. Elements such as zinc, copper, gold or lead ions are known to react specifically with sulfur. However, copper exhibits an unfavourable reaction with oxygen, to form copper oxide, while gold proves to be potentially complex to handle.

A known method for the detection of $H_2S$ consists in using a paper impregnated with lead acetate $Pb(CH_3COO)_2$ and is described in the paper by T. Ding, J.-R. Zhang, S. Long and J.-J. Zhu, Synthesis of HgS and PbS nanocrystals in a polyol solvent by microwave heating, *Microelectronic Engineering*, 66, 46-52, 2003. In this case, the molecule does not exhibit the ability to be polymerized and only impregnates the paper.

One method of production of this compound is the reaction of a Pb(II) cation with acetic acid in a basic medium.

The reaction of the product thus formed with $H_2S$ brings about the conversion into Pb(II) sulfide, PbS, a grey precipitate, according to the reaction:

The affinity of sulfur for the Pb(II) cations is very strong. It makes it possible, for example, to form PbS nanoparticles from solid sulfur, sulfide anions or $H_2S$, as described in the papers by T. Ding, J.-R. Zhang, S. Long and J.-J. Zhu, Synthesis of HgS and PbS nanocrystals in a polyol solvent by microwave heating, *Microelectronic Engineering*, 66, 46-52, 2003, by H. Karami, M. Ghasemi and S. Matini, Synthesis, characterization and application of lead sulfide nano-structures as ammonia gas sensing agent, *Int. J. Electrochem. Sci.*, 8, 11661-11679, 2013, and by Z. Zeng, S. Wang and S. Yang, Synthesis and characterization of PbS nanocrystallites in random copolymer ionomers, *Chem. Mater.*, 11, 3365-3369, 1999.

More specifically, in order to be able in particular to produce a sensor of acoustic wave passive sensor type, the Applicants provide a solution which consists of a polymer film which allows the Pb or Zn cations to impregnate a solid matrix intended to act as sensitive layer and which is compatible with the preparation of an acoustic wave passive sensor.

SUMMARY OF THE INVENTION

A subject-matter of the present invention is thus a $H_2S$ sensor, comprising at least one acoustic wave transducer and a film comprising a polymer matrix comprising carboxylate functional groups and lead or zinc cations.

The film represents the sensitive layer of the sensor.

According to alternative forms, the sensor comprises an antenna which makes it possible to remotely interrogate the said sensor and to thus produce a remotely interrogatable passive sensor.

The polymer film can typically exhibit a thickness of between about a hundred nanometres and a few microns.

According to alternative forms of the invention, the polymer corresponds to the following chemical formulae:

-continued with X = Pb or Zn with n, m and p integers.

In order to obtain the sensitive layer of polymer film, the Applicants have developed polymers incorporating the necessary functional groups, that is to say incorporating lead or zinc and carboxylate functional groups, and more specifically, for example, for this, families of molecules of the type: $(R_1COO) \times (R_2COO)$ where $R_1$ and $R_2$ denote groups having reactive functional groups which make it possible to link the Pb(II) cations or the Zn(II) cations by its ligands in macromolecules.

In order to maximize the sensitivity of the organic layer, it is advantageous to maximize the density of Pb(II) ions or of Zn(II) ions in the matrix by preferably reducing as much as possible the length of the carbon-based chains of the monomers.

The Applicants have started from the observation that the functionalization must, on the one hand, affect as little as possible the propagation of the acoustic wave in the absence of $H_2S$ but also offer sufficient reactive sites to induce a significant variation, for example in the speed of the acoustic wave, in the presence of $H_2S$.

This compromise and also the control of the thickness of the layer and the density of the receptor sites can be optimized. Thus, in order to limit, on the one hand, the perturbation induced by the polymer film on the propagation of the acoustic wave, while maximizing, on the other hand, the variation in the speed of the wave by variation of the limiting conditions of propagation, it is particularly advantageous to use a film thickness of the order of 1 to 5% of the acoustic wavelength. For a working frequency of 150 MHz, for example, such a condition results in a film thickness of between approximately 250 nm and 5 μm.

It should be noted that this is because the same thickness ranges can be employed whether a surface wave transducer or volume wave transducer is concerned. As the thickness varies as the inverse of the root of the frequency, to change from a volume wave resonator (working frequency typically of the order of 5-10 MHz) to an acoustic wave transducer (working frequency typically of the order of 1 GHz) varies the film thickness only by a factor of 10.

According to alternative forms of the invention, the transducer is a surface acoustic wave transducer.

According to alternative forms of the invention, the sensor comprises a delay line comprising at least one surface acoustic wave transducer and a mirror, the sensitive layer being positioned between the said transducer and the said mirror. Advantageously, the delay line comprises a transducer positioned between two mirrors, the said sensitive layer being positioned between the said transducer and one of the said mirrors.

According to alternative forms of the invention, the transducer is a volume wave or Lamb wave transducer.

Advantageously, the transducer incorporated in the sensor is a dipole, whether it comprises a delay line architecture or a resonator propagating an acoustic wave.

According to alternative forms of the invention, the transducer comprises a substrate made of lithium niobate or made of lithium tantalate.

Another subject-matter of the invention is a process for the manufacture of a sensor according to the invention, comprising the following steps:

the deposition at the surface of a substrate of monomer containing a lead or zinc carboxylate complex and a polymerizable functional group, which can, for example, be of chemical formula:

with X: $Pb^{2+}$ or $Zn^{2+}$ the polymerization of the said monomer.

A further subject-matter of the invention is a process for the manufacture of a sensor according to the invention, comprising the deposition on a substrate of a polymer film, synthesized beforehand, which can be of chemical formula:

with X: $Pb^{2+}$ or $Zn^{2+}$ with n, m and p integers.

Another subject-matter of the invention is a process for the manufacture of a sensor according to the invention, comprising the deposition on a substrate of a polymer film obtained by polycondensation or polyaddition or polyelimination between a monomer containing a lead or zinc carboxylate complex and a difunctional molecule. The final polymer can be of chemical formula:

with X: $Pb^{2+}$ or $Zn^{2+}$ with n, m and p integers.

A further subject-matter of the invention is a $H_2S$ detection device comprising:
a sensor according to the invention;
radiofrequency interrogation means;
means for detecting the response of the said sensor.

According to alternative forms of the invention, the device comprises means for analysis of the speed or of the insertion losses of the acoustic wave in order to identify the presence of the compound $H_2S$.

BRIEF DESCRIPTION OF THE DRAWINGS

A better understanding of the invention will be obtained and other advantages will become apparent on reading the description which will follow, given without limitation, and by virtue of the figures, among which.

DETAILED DESCRIPTION

The $H_2S$ sensor according to the invention can be a wire-based sensor or a remotely interrogatable passive sensor.

The film sensitive to $H_2S$ can advantageously be thus combined with an acoustic wave transducer in order to produce a remotely interrogatable passive sensor according to the invention, the acoustic wave transducer being capable of converting an electromagnetic signal into mechanical vibration.

Figure 1A:
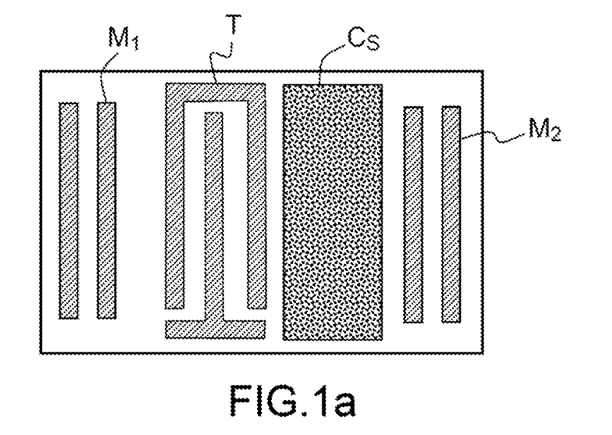
FIGS. 1a and 1b illustrate an example of surface acoustic wave sensor according to the present invention and a test configuration using surface acoustic wave transducers.

FIG. 1a illustrates an example of surface acoustic wave sensor of the invention, of compact configuration.

The sensor comprises a reflective delay line, exhibiting two mirrors $M_1$ and $M_2$, and a transducer T located between the two mirrors.

It can be particularly advantageous for the sensor to incorporate an acoustic wave transducer connected to an antenna and several mirrors, thus making it possible to carry out a multiparameter measurement as described in the paper: J. Micro/Nanolith, MEMS MOEMS, 8(3), 031306 (2009)— Wireless surface acoustic wave chemical sensor for simultaneous measurement of $CO_2$ and humidity.

Typically, the transducer can conventionally comprise interdigitated electrodes.

The presence of two mirrors makes it possible to have a reference zone, without which the $H_2S$ measurement is contaminated by the variation in reader-sensor distance.

It is thus useful to have available a sensitive zone for the measurement and a zone free of surface functionalization in order to establish the RADAR-sensor distance.

A layer $C_s$ of polymer film sensitive to $H_2S$ is deposited between the transducer and one of the mirrors. More specifically, in this mirror-transducer-mirror architecture, the zone separating the first mirror from the transducer is free of any surface functionalization in order to establish the time of flight in free space of the acoustic wave (whatever the gas concentration), whereas the second region between the transducer and the second mirror is functionalized in order to vary the speed of the acoustic wave with the absorption of the gas.

For a wireless measurement in a reflective delay line configuration, strongly coupled substrates (coupling coefficient of greater than 1%), such as lithium niobate or lithium tantalate, are favoured.

Figure 1B:
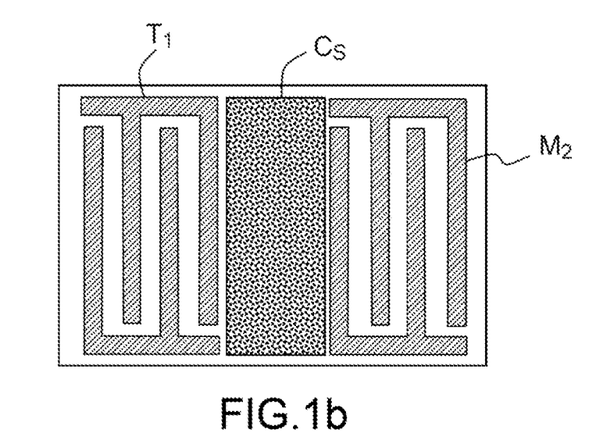

FIG. 1b for its part illustrates a simple configuration comprising two surface acoustic wave transducers $T_1$ and $T_2$, between which is positioned a sensitive layer $C_s$ of polymer film. Such a configuration has been used by the Applicant to experimentally validate the sensitivity of the thin polymer film used in the present invention to the detection of $H_2S$, as will be explained subsequently.

The transducer employed in the passive sensor of the invention can also be a volume wave or Lamb wave transducer, the surface wave transducers being all the same more advantageous in terms of frequency rise necessary for the reduction of antennae of the emitter and of the receiver.

Figure 2A:
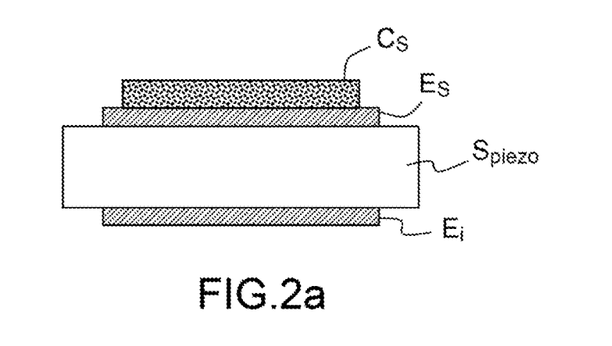
FIGS. 2a and 2b illustrate examples of volume wave sensor according to the present invention.
Figure 2B:
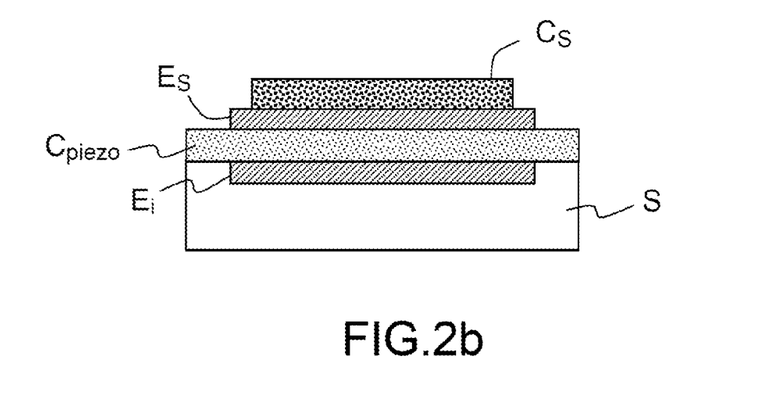

Alternative forms of volume wave transducers are represented in FIGS. 2a and 2b.

These transducers can be of cylindrical symmetry geometry.

FIG. 2a illustrates a first configuration exhibiting an electrode $E_s$ covered with a sensitive layer $C_s$, a piezoelectric substrate $S_{piezo}$ being inserted between the upper electrode $E_s$ and a lower electrode $E_i$.

FIG. 2b illustrates a second configuration exhibiting a thin piezoelectric substrate $C_{piezo}$ deposited on a substrate S exhibiting low elastic losses, two electrodes $E_s$ and $E_i$ (buried electrode) surrounding the thin substrate, so as to constitute the volume wave transducer. The sensitive layer $C_s$ is deposited at the surface of the upper electrode $E_s$.

The sensor thus produced can be remotely interrogated and the response carries information of detection of the presence of $H_2S$.

Figure 3:
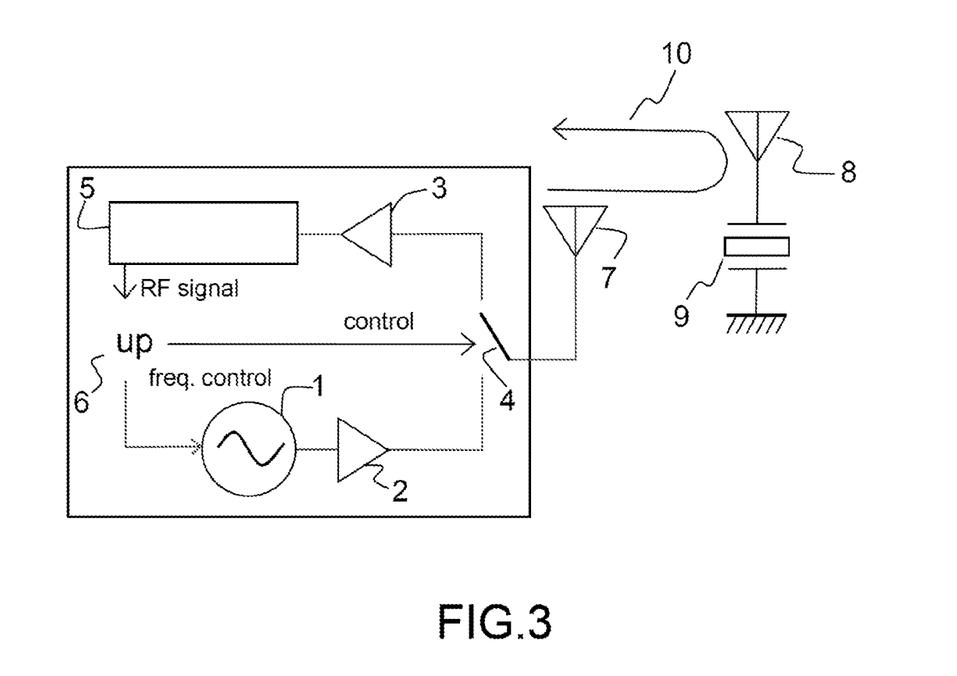
FIG. 3 illustrates a remotely interrogatable sensor reading architecture according to the invention.

FIG. 3 illustrates, as such, an example of typical architecture of acoustic wave transducer reader interrogated by a wireless link to a radiofrequency carrier.

A carrier is generated by a source 1 and amplified by an amplifier 2 before being emitted through a switch 4.

A pulse is formed by switching the switch between the source and the receive stage formed of a low-noise amplifier 3 and of a phase and magnitude (I/Q) detector 5.

An antenna 7 linked to the common point 4 radiates the signal 10, which remotely powers, through an antenna 8, the passive sensor 9 comprising the film sensitive to $H_2S$. In FIG. 3, the passive sensor is represented diagrammatically by a representation of a resonator (even in the case of the use of a delay line).

The response of the sensor 9 carries the signature of the detection of the chemical compound $H_2S$, whether it concerns time of flight of the acoustic wave (in the case of a delay line) or a variation in resonance frequency, in the case of a sensor comprising a resonator.

The reference up relates to an example of microcontroller, an $STM_{32}F_{103}$, but the exact type of microcontroller has no effect; the role of this microcontroller is to sequence the various measurement steps, without constraint of computational power. It might be an FPGA component, a DSP component or any programmable digital component capable of sequencing the measurements.

In order to obtain the sensitive layer consisting of the polymer film, the Applicants have thus developed polymers incorporating the necessary functional groups. In particular, they have developed, for this, families of molecules of the type: $(R_1COO) \times (R_2COO)$ where $R_1$ and $R_2$ denote groups having reactive functional groups which make it possible to link the cations by its ligands in macromolecules, and X denotes a $Pb^{2+}$ cation or a $Zn^{2+}$ cation.

Several examples of the synthesis of polymers used in the present invention are presented below:

First Synthesis Example

The first synthesis is based on the formation of a lead (II) or zinc(II) carboxylate complex containing a polymerizable functional group constituting a soluble monomer which can be deposited in the form of a thin film on a substrate.

These monomers are then polymerized under the effect of an external stimulus (heat, photons) in order to obtain a crosslinked film.

with X: $Pb^{2+}$ or $Zn^{2+}$

Second Synthesis Example

This second synthesis is based on the complexing of Pb(II) or Zn(II) cations by a polymer containing pendant carboxylic acid functional groups. Subsequently, the polymer is deposited in the form of a thin film on a substrate:

with X: $Pb^{2+}$ or $Zn^{2+}$

Third Synthesis Example

This third synthesis example is based on the complexing of Pb(II) or Zn(II) cations by polyfunctional molecules which can subsequently react, by polycondensation, polyaddition or polyelimination (or any other combination of these reactions), with complementary polyfunctional molecules in order to form a thin polymer film on a substrate, for example according to the following reaction scheme:

with X: $Pb^{2+}$ or $Zn^{2+}$

In the different cases, the thin films, subsequently subjected to exposure to $H_2S$ gas, can generate the formation of lead (II) or zinc(II) sulfide, i.e. PbS or ZnS.

In the context of the present invention, the formation of PbS or ZnS results in a variation in weight, accompanied by a change in colour.

The relative variation in weight, which is the essential parameter in the acoustic detection, depends directly on the choice of the organic precursors of the matrix.

If the starting monomer is acrylic acid, its molar mass is 72 g/mol. As the molar mass of lead is 207 g/mol, the complexing of the sensitive layer by $H_2S$ (molar mass 34 g/mol) results in a relative variation in weight of $34/(207+72 \times 2) = 10\%$.

It should be noted that, generally, a surface acoustic wave transducer is known to be capable of detecting a variation in weight of the order of a few tens of $ng/cm^2$, defining the detection limit accessible by means of this type of transducer.

The Applicants have carried out tests making it possible to validate the concept of sensor of the present invention and the choice of the sensitive layer actually making possible detection of $H_2S$, in an acoustic wave passive sensor which can be remotely interrogated.

This experimental demonstration of concept of sensor is based on four steps:

Step 1: the synthesis and the characterization of the molecules sensitive to $H_2S$. The sensitivity to $H_2S$ is tested by direct exposure of the molecules to $H_2S$ triggering a change in colour;

Step 2: the preparation of a thin transparent film on a glass slide and the study of the solid-phase polymerization of the molecules;

Step 3: the detection of a change in absorbance of this thin film during exposure to $H_2S$;

Step 4: the deposition of a thin film on a surface acoustic wave transducer in order to estimate the variation in the speed of the acoustic wave during the exposure of the molecules to $H_2S$.

To start with, lead (II) complexes were synthesized and characterized by the standard methods of analytical chemistry, making possible the preparation of several grams of molecules in each synthesis.

The $H_2S$ which is used for the tests is produced by an acid treatment of a sulfur salt. The first test consisted of the exposure of the powder of lead (II) complexes to a stream of $H_2S$ gas under standard conditions.

The reaction appears within a time interval which is less than the period of time between two photographs extracted from a 50 images/second film, virtually instantaneously and probably limited by the diffusion time of the gas. The change in colour—from a white powder to a black powder—is visible on the sample of powder located at the bottom of the container.

Having validated the reactivity of the synthesized compound with $H_2S$, the deposition of the molecule, dissolved in dimethyl sulfoxide (DMSO), is obtained by evaporation of the solvent, commonly known as "drop casting".

The quality of the polymerization is validated by the mechanical strength of the film.

Once the film has formed on the glass slide, the change in colour also validates the reactivity of the film during the exposure to $H_2S$. The Applicants have validated that thin polymer films are obtained by spin coating on silicon substrates. The samples used exhibit surface areas of the order of 5 to 10 $cm^2$. The sets of parameters (solvent, viscosity, temperature, rotational speed) were optimized in order to determine robust and reproducible protocols for obtaining thin layers of controlled thickness between 0.5 and 2 microns. The Applicants then confirmed that these films were still sensitive to the presence of $H_2S$. When these films are exposed to $H_2S$, a change in colour is visible.

Finally, the deposition procedure is reproduced on a surface acoustic wave transducer in transmission (quartz substrate propagating a Love wave). Such a device does not propagate the same wave nature as a reflective delay line on lithium niobate, which can advantageously be used for a wireless radiofrequency measurement, but its behaviour is suitably controlled and makes possible a fine analysis of the behaviour of the thin organic film subjected to $H_2S$.

Figure 4A:
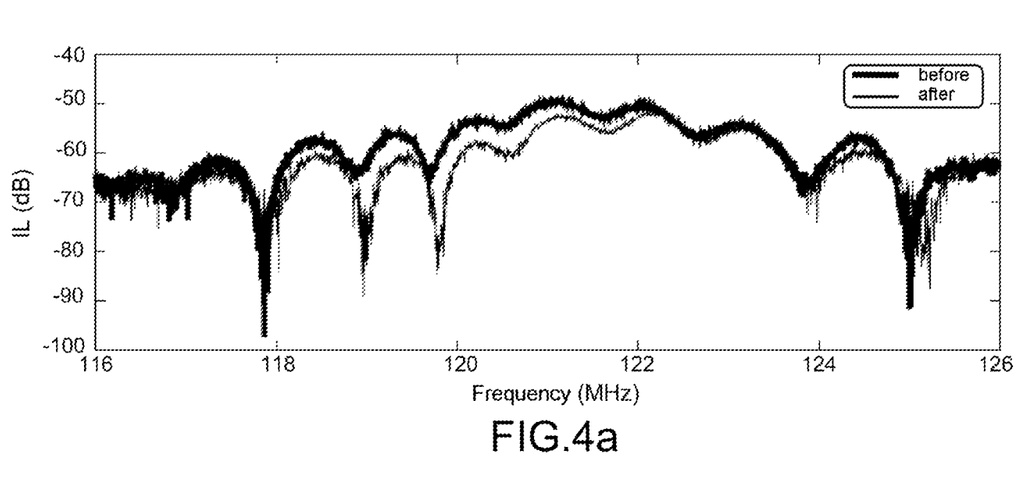
FIGS. 4a and 4b illustrate response curves in terms of magnitude and of phase of a sensor according to the invention, as a function of the interrogation frequency (before and after functionalization by $H_2S$ of the sensitive layer).
Figure 4B:
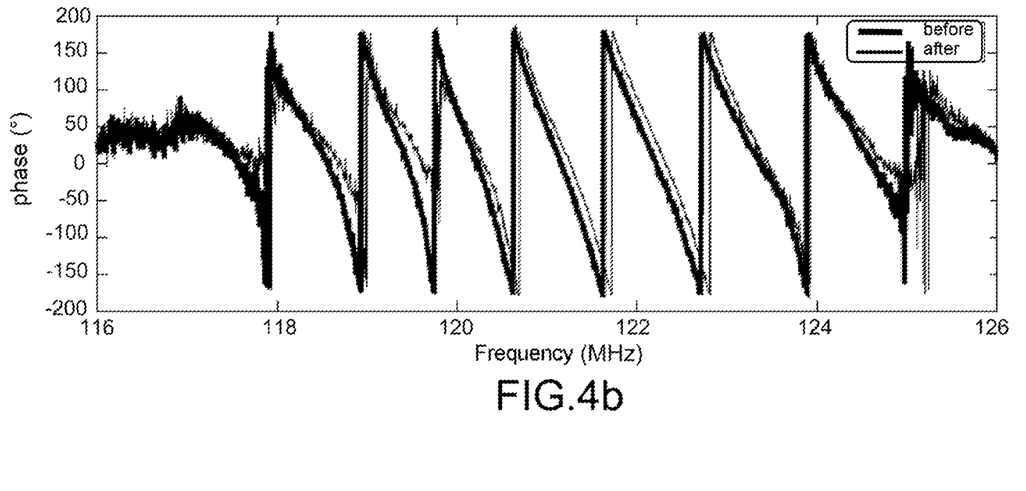

FIGS. 4a and 4b illustrate the results of the measurements for determination of the magnitude IL and of the phase as a function of the interrogation frequency, before functionalization and after functionalization of the polymer, result of the exposure to $H_2S$ (before functionalization, each delay line exhibits an attenuation of the order of 23 dB. The deposition of the film brings about a significant attenuation dependent on the thickness of the film), and the change in the phase of the signal.

The curves in thick line relate to these parameters measured before reaction with $H_2S$, the curves in fine line relating to these parameters obtained after reaction.

The change in the phase towards high frequencies is a priori surprising as an increase in the weight of the film is generally reflected by a shift of the curves towards low frequencies.

In the case of a rise in the speed of the acoustic wave (observed as shift of the curve towards high frequencies), the conventional interpretation is to attribute this rise in speed to a stiffening of the adsorbed organic layer.

The Applicants attribute this effect to the change of the lead, in a form of ions in the matrix, to a form of PbS nanoparticles in the organic matrix.

This behaviour (increase in the speed) is relatively unusual in detection of gaseous compounds by a thin organic layer.

A major advantage of this observation is that of providing a clear distinction between detection of $H_2S$ and interference by non-specific absorption of other chemical entities present in the atmosphere: these inducing a variation in weight of the film—without stiffening it—which is reflected by a fall in the speed of the acoustic wave (or a decrease in the phase if the transducer is probed at a fixed frequency).

The risk of a false positive is thus reduced by this analysis.

The variation of close to 20° in the phase during the exposure to $H_2S$ is significant and regarded as constituting a very readily detectable signal. For reference, the paper by D. Rabus, J.-M. Friedt, S. Ballandras, G. Martin, E. Carry and V. Blondeau-Patissier, A high sensitivity open loop electronics for gravimetric acoustic wave-based sensors, *IEEE Trans. UFFC*, 60(6), 1219-1226, 2013, demonstrates a detection limit more than 500 times lower (in a delay line in transmission context).

The invention claimed is:

1. An $H_2S$ sensor, comprising at least one acoustic wave transducer and a film comprising a polymer matrix having covalently bound pendant carboxylate functional groups complexed with zinc cations.

2. The sensor according to claim 1, comprising an antenna which makes it possible to remotely interrogate the sensor.

3. The sensor according to claim 1, wherein the film exhibits a thickness of between a hundred nanometres and 2 microns.

4. The sensor according to claim 1, wherein the polymer corresponds to the following chemical formula:

with X: $Zn^{2+}$ with n, m and p integers.

5. The sensor according to claim 1, wherein the polymer corresponds to the following chemical formula:

with X: $Zn^{2+}$ with n, m and p integers.

6. The sensor according to claim 1, wherein the polymer corresponds to the following chemical formula:

with X: $Zn^{2+}$ with n, m and p integers.

7. The sensor according to claim 1, wherein the film exhibits a thickness of between 1 and 5% of the acoustic wavelength.

8. The sensor according to claim 7, wherein the film exhibits a thickness of between 250 nm and 5 um.

9. The sensor according to claim 1, wherein the transducer is a surface acoustic wave transducer.

10. The sensor according to claim 9, comprising a delay line comprising the surface acoustic wave transducer and a mirror.

11. The sensor according to claim 9, comprising a transducer positioned between two mirrors, the said sensitive layer being positioned between the said transducer and one of the said mirrors.

12. The sensor according to claim 1, wherein the transducer is a volume acoustic wave or Lamb acoustic wave transducer.

13. The sensor according to claim 1, wherein the transducer comprises a substrate made of lithium niobate or made of lithium tantalate.

14. An $H_2S$ detection device comprising:
a sensor according to claim 1;
a radiofrequency interrogation means;
a means for detecting the response of the said sensor.

15. The device according to claim 14, comprising a means for analysis of the speed or of the insertion losses of the acoustic wave in order to identify the presence of the compound $H_2S$.

16. An $H_2S$ sensor comprising:
an acoustic wave transducer;
a film including a polymer matrix having covalently bound pendant carboxylate functional groups complexed with lead or zinc cations, wherein the film exhibits a thickness of between 1 and 5% of the acoustic wavelength; and
an antenna for remotely interrogating the sensor.

17. An $H_2S$ sensor comprising:
an acoustic wave transducer;
a film including a polymer matrix having covalently bound pendant carboxylate functional groups complexed with lead or zinc cations, wherein the polymer corresponds to the following chemical formula:

with X: $Pb^{2+}$ or $Zn^{2+}$ with n, m and p integers, wherein the film exhibits a thickness of between 1 and 5% of the acoustic wavelength; and
an antenna for remotely interrogating the sensor.

* * * * *